(12) United States Patent
Kaya et al.

(10) Patent No.: US 9,933,366 B2
(45) Date of Patent: Apr. 3, 2018

(54) ASSAY METHOD USING SURFACE PLASMON-FIELD ENHANCED FLUORESCENCE SPECTROSCOPY

(71) Applicant: Konica Minolta, Inc., Chiyoda-ku, Tokyo (JP)

(72) Inventors: Takatoshi Kaya, Inagi (JP); Makiko Ootani, Tokyo (JP)

(73) Assignee: KONICA MINOLTA, INC., Chiyoda-Ku, Tokyo (JP)

( * ) Notice: Subject to any disclaimer, the term of this patent is extended or adjusted under 35 U.S.C. 154(b) by 270 days.

(21) Appl. No.: 14/435,867

(22) PCT Filed: Oct. 17, 2013

(86) PCT No.: PCT/JP2013/078207
§ 371 (c)(1),
(2) Date: Apr. 15, 2015

(87) PCT Pub. No.: WO2014/061743
PCT Pub. Date: Apr. 24, 2014

(65) Prior Publication Data
US 2015/0268167 A1    Sep. 24, 2015

(30) Foreign Application Priority Data
Oct. 18, 2012  (JP) ................ 2012-230893

(51) Int. Cl.
*G01N 21/64* (2006.01)
*G01N 33/543* (2006.01)
*G01N 33/569* (2006.01)

(52) U.S. Cl.
CPC ..... *G01N 21/648* (2013.01); *G01N 33/54306* (2013.01); *G01N 33/56966* (2013.01); *G01N 2021/6439* (2013.01)

(58) Field of Classification Search
CPC .......... G01N 21/648; G01N 33/54306; G01N 33/56966; G01N 2021/6439
See application file for complete search history.

(56) References Cited

U.S. PATENT DOCUMENTS

2011/0097740 A1    4/2011  Paek et al.
2015/0260654 A1*   9/2015  Ootani ................ G01N 21/553
                                              435/7.1

FOREIGN PATENT DOCUMENTS

JP        02287260 A    11/1990
JP      2008261733 A    10/2008
(Continued)

OTHER PUBLICATIONS

Matveeva et al. Red blood cells do not attenuate the SPCE fluorescence in surface assays. Anal Bioanal Chem 388: 1127-1135 (2007).*

(Continued)

*Primary Examiner* — Gailene Gabel
(74) *Attorney, Agent, or Firm* — Cantor Colburn LLP (57) ABSTRACT

Provided is an assay method utilizing surface plasmon-field enhanced fluorescence spectroscopy, which suppresses fluctuations in an absolute value of a background signal that is referred to as a resonance angle or an optical blank by improving the effect when a whole blood sample is used, specifically, the effect by the blood cell components remaining in a measurement liquid during a SPFS measurement, with regards to a photometric condition setting step, which is a characteristic step in assay methods utilizing SPFS. The above-mentioned problem is solved by an assay method utilizing surface plasmon-field enhanced fluorescence spectroscopy, including a primary reaction step of a sample, a first washing step, a labeling reaction step, and a measurement step, wherein the method includes a step for evaluating (Continued)

a blood cell component quantity between the primary reaction step and the labeling reaction step.

15 Claims, 3 Drawing Sheets

(56) References Cited

FOREIGN PATENT DOCUMENTS

| JP | 2011149831 A | 8/2011 | | |
|---|---|---|---|---|
| JP | 2011524982 A | 9/2011 | | |
| WO | WO 2011111472 | * | 9/2011 | ........... G01N 21/553 |

OTHER PUBLICATIONS

Evgenia Matveeva et al.,"Red blood cells do not attenuate the SPCE fluorescence in surface assays", Analytical and Bioanalytical Chemistry, Jul. 2007, vol. 388, Issue 5, pp. 1127-1135.
Extended European Search Report corresponding to Application No. 13848099.1-1554/2910947 PCT/JP2013/078207, dated May 10, 2016.
International Search Report correspondng to Application No. PCT/JP2013/078207; dated Jan. 28, 2014, with English translation.
Written Opinion of the International Searching Authority corresponding to International application No. PCT/JP2013/078207; dated Jan. 28, 2014, with English translation.

* cited by examiner

BLOOD CELL COMPONENT RESIDUAL RATE (%)

ASSAY METHOD USING SURFACE PLASMON-FIELD ENHANCED FLUORESCENCE SPECTROSCOPY

CROSS REFERENCE TO RELATED APPLICATIONS

This is the U.S. national stage of application No. PCT/JP2013/078207, filed on Oct. 17, 2013. Priority under 35 U.S.C. § 119 (a) and 35 U.S.C. § 365(b) is claimed from Japanese Application No. 2012-230893, filed Oct. 18, 2012, the disclosure of which is also incorporated herein by reference.

TECHNICAL FIELD

The present invention relates to an assay method utilizing surface plasmon-field enhanced fluorescence spectroscopy (SPFS: Surface Plasmon-field enhanced Fluorescence Spectroscopy), and especially relates to an assay method utilizing SPFS intended for a whole blood sample.

BACKGROUND ART

A biochemical examination of blood is generally conducted on plasma or serum as a subject. Plasma is prepared by collecting about 10 mL of venous blood by a syringe and centrifuging the venous blood. In an immune examination of an item relating to infectious diseases, serum is used as a measuring sample, but at least about 30 minutes of treatment time for separating serum, which is the sum of a time for solidifying blood and a time for the subsequent centrifugation, is required for obtaining serum from whole blood.

Therefore, medical staffs require great care and time, and this is sometimes harmful to the life of a patient especially in an emergency case such as a cardiac disease. Furthermore, in an emergency operation in which an immediate judgment to determine whether or not a patient has an infectious disease such as hepatitis or HIV is required, the development of a more rapid measuring method in which an examination time from after collection of blood is shorten has been desired.

Examples of immune assays include a radioimmunoassay (RIA), an enzyme immunoassay (EIA), a particle agglutination process, a counting immunoassay and the like, and in RIA and EIA, it is necessary to conduct an antigen-antibody reaction and then conduct B/F separation, and thus great care and time are required until a measuring result is obtained.

Conventionally, in carrying out an immunoassay intended for an antigen and the like in blood, a sample in which a certain defined amount of plasma or serum accounts for 100% is envisaged. Therefore, in the case of a sample containing blood cell components such as whole blood, the serum or plasma component to be measured is apparently small (35 to 65% of whole blood differs in cell components in individuals). Accordingly, in conventional methods, a measurement value of an antigen or the like contained in blood is corrected and a final quantification value is calculated in some cases with consideration for the amount of the above-mentioned blood cell components, but it has not been carried out until now to apply the exemplary embodiments of other steps to the case when a sample containing blood cell components such as whole blood is used.

Patent Literature 1 suggests an automatic analyzer having a washing function, which can retain the state of the automatic analyzer always constant by monitoring the state of the automatic analyzer and automatically determining the degree of washing by reflecting the state.

This automatic analyzer is an automatic analyzer that can automatically conduct an analysis and can conduct washing motions, and includes a measurement result monitoring means for monitoring at least one of items of change in a water blank value, stability of a reagent blank value and an analysis result of a control subject among measurement results of a light absorbance measuring unit, and a washing condition determination means for determining a washing condition from the result of the measurement result monitoring means and a standard value. Therefore, the invention is an invention that pays an attention to contamination among samples with consideration for sample crosstalk during continuous measurement of samples, and is required in an apparatus to which an immobilized dispenser nozzle is adopted. However, various means used for such automatic analyzer are not disclosed as means for use in conducting an immunoassay using a sample containing blood cell components such as whole blood.

CITATION LIST

Patent Literature

Patent Literature 1: JP 2-287260 A

SUMMARY OF INVENTION

Technical Problem

The object of the present invention is to suppress fluctuations in an absolute value of a background signal that is referred to as a resonance angle or an optical blank by improving the effect when a whole blood sample is used, specifically, the effect by blood cell components remaining in a measurement liquid during SPFS measurement, with regards to a photometric condition setting step, which is a characteristic step in assay methods utilizing SPFS.

Solution to Problem

With respect to fluctuations of photometric conditions in a measurement by a surface plasmon-field enhanced fluorescence spectroscopy (SPFS) intended for a whole blood sample, the present inventors have considered about a SPFS assay sequence intended for a whole blood sample. During the process thereof, they have found an assay method utilizing SPFS by which fluctuations of a measurement liquid during a photometric condition setting step in a SPFS measurement are significantly suppressed and a photometric condition of a SPFS measurement in which fluctuations derived from blood cell components are suppressed, by, for example, an assay sequence in which at least one step for evaluating a blood cell component quantity is incorporated between a primary reaction step using a whole blood sample and a labeling reaction step, and completed the present invention.

The step for evaluating a blood cell component quantity as mentioned above is an assay sequence that is characteristic to a SPFS measurement that requires presetting of a photometric condition before a final signal measurement step, and is a principally unnecessary step in conventional immunoassay methods other than SPFS; therefore, it is an essential step that is characteristic to an assay method utilizing SPFS intended for a whole blood sample.

In order to attain at least one of the above-mentioned purposes, an assay method utilizing surface plasmon-field enhanced fluorescence spectroscopy reflecting an aspect of the present invention is an assay method utilizing surface plasmon-field enhanced fluorescence spectroscopy, including a primary reaction step of a sample, a subsequent first washing step, a labeling reaction step and a measurement step, wherein the method includes a step for evaluating a blood cell component quantity between the primary reaction step and the labeling reaction step.

Advantageous Effects of Invention

Accordingly, according to the assay method utilizing SPFS according to the present invention, the fluctuations of a measurement liquid during a photometric condition setting step for a SPFS measurement are significantly suppressed, by an assay sequence in which at least one step for evaluating a blood cell component quantity is incorporated between a primary reaction step and a labeling reaction step, and thus it becomes possible to obtain a photometric condition of a SPFS measurement in which fluctuations derived from blood cell component are suppressed.

DESCRIPTION OF EMBODIMENTS

The assay method utilizing SPFS according to the present invention is an assay method utilizing SPFS including a primary reaction step of a sample, a first washing step, a labeling reaction step, and a measurement step, wherein the method includes a step for evaluating a blood cell component quantity between the primary reaction step and the labeling reaction step.

According to this invention, since the prepared sample sequentially undergoes the primary reaction step, the first washing step, and the at least one step for evaluating the blood cell component quantity during or after the first washing step, and then undergoes the labeling reaction step and the measurement step, the effect when a whole blood sample is used can be improved with regards to a photometric condition setting step, which is a characteristic step in a measurement in an assay method utilizing SPFS. Furthermore, the problem of fluctuations in an absolute value of a background signal that is referred to as a resonance angle or an optical blank of surface plasmon by blood cell components remaining in a measurement liquid during a photometric condition setting step for a SPFS measurement can be solved. In addition, in a biological examination of blood, the time and effort for centrifuging the blood is eliminated, and thus it becomes possible to save the life of a patient having urgency of a cardiac disease or the like.

More preferable is an assay method utilizing SPFS, including a primary reaction step for bringing an analyte in a sample into contact with a ligand immobilized on a sensor substrate having a metal thin film, a first washing step for washing the sensor substrate after the primary reaction step, a labeling reaction step for bringing the analyte captured by the ligand by the primary reaction step after the first washing step into contact with a fluorescence-labeled labeled ligand, a measurement step for measuring the fluorescence of the labeled ligand captured on the sensor substrate after the labeling reaction step, wherein a step for evaluating a blood cell component quantity for conducting an evaluation relating to the blood cell component quantity remaining on the sensor substrate is conducted between the primary reaction step and the labeling reaction step.

In the assay method utilizing SPFS according to the present invention, it is preferable to repeat the first washing step until the index that reflects the blood cell component quantity in the evaluation step reaches a predetermined value.

In the assay method utilizing SPFS according to the present invention, it is preferable that the index that reflects the blood cell component quantity is a measurement value of a light absorbance.

In the assay method utilizing SPFS according to the present invention, the subject to be evaluated of the blood cell component quantity in the evaluation step is preferably a washing liquid in the first washing step. The washing liquid in the first washing step may be either an internal liquid in a sensor chip, or a waste liquid discharged from the sensor chip.

In the assay method utilizing SPFS according to the present invention, in the case when the evaluation step is conducted after the first washing step, the index that reflects the blood cell component quantity in the evaluation step is a measurement value of a light absorbance, and the measurement value of a light absorbance goes beyond a predetermined value, it is preferable to conduct the first washing step again.

It is preferable that the assay system utilizing SPFS according to the present invention is a system that conducts the assay method utilizing SPFS mentioned above, and includes a spectrometer mentioned below.

Specific embodiments for carrying out the assay method utilizing SPFS according to the present invention (and the assay system) will be explained below in detail. The present invention is not limited to the following embodiments, and can be carried out with various modifications within the scope of the gist thereof.

<Assay Method Utilizing SPFS>

Figure 1:
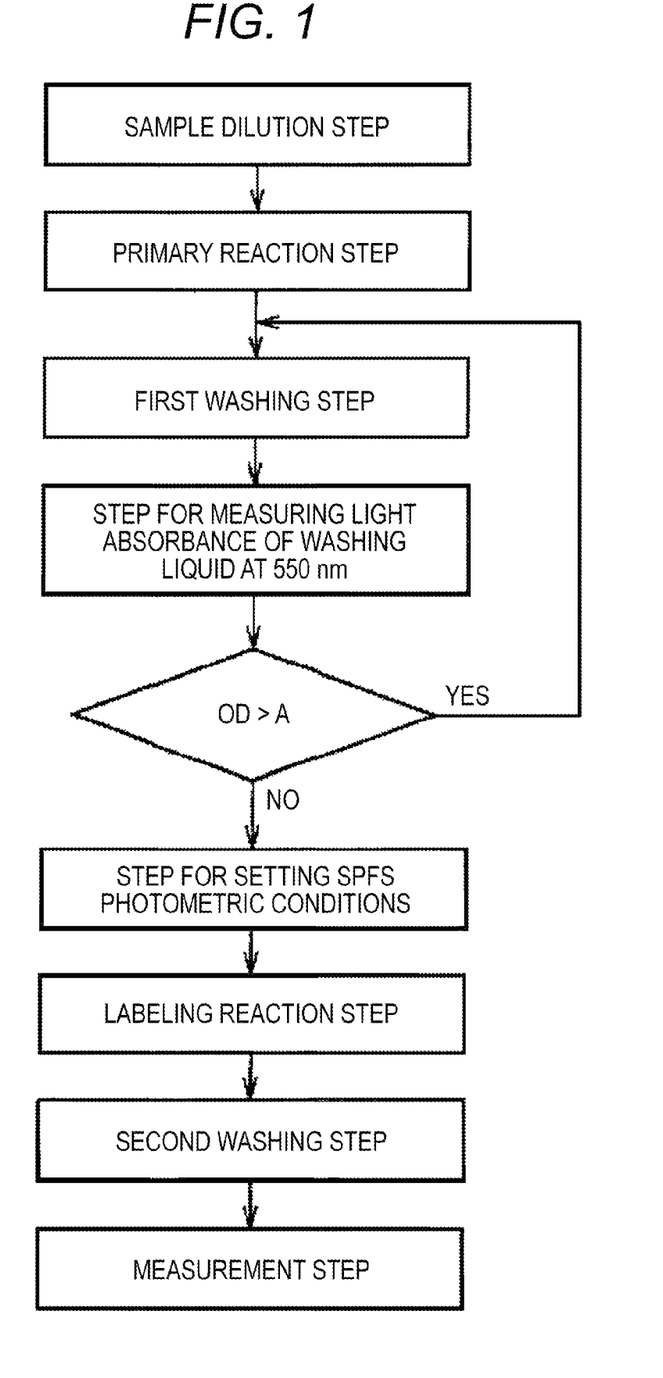
FIG. 1 is a flow chart showing an exemplary embodiment of an assay method utilizing SPFS according to the present invention.

As shown in FIG. 1, in a major flow of the assay method utilizing SPFS in this exemplary embodiment, a sample dilution step, a primary reaction step, a first washing step, a step for evaluating a blood cell component quantity, a step for setting SPFS photometric measurement conditions, a labeling reaction step, a second washing step and a measurement step are sequentially conducted. The respective steps will be sequentially explained below, by using an embodiment in which a flow path is formed on a sensor substrate, and respective samples and reagents are fed so as to be brought into contact with the sensor substrate through the flow path. Furthermore, in the following explanation, a chip-like sensor substrate in which a well shape and a flow path shape are incorporated in and integrated with a sensor substrate is also referred to as a sensor chip.

(Sample Dilution Step)

The sample dilution step is a step for diluting a sample so that the respective steps relating to the measuring of SPFS can be suitably conducted. The dilution rate of the sample is not especially limited, and can be suitably set depending on the exemplary embodiment of the measuring system, the amount of the collected sample, the flow amount in the liquid sending to the sensor substrate, the viscosity of the sample (the blood cell component quantity in whole blood) and the like, and is generally from 0 to 100 times, preferably from 2 to 20 times. The dilution method is also not especially limited, and a suitable amount of solvent (PBS (phosphate buffer saline), TBS (tris buffer saline) and the like) may be added as a dilution liquid to the sample according to a conventional method.

(Primary Reaction Step)

The primary reaction step is a step for bringing the sample into contact with a sensor substrate. By this step, a complex of an analyte (antigen) and a ligand (antibody) immobilized on the surface of the sensor substrate is formed.

The time for the primary reaction step, i.e., the time for bringing the sample into contact with the sensor substrate by liquid sending is adjusted depending on the amount of the analyte included in the sample and the like in some cases, and is generally from 0.5 to 90 minutes, preferably generally from 5 to 60 minutes.

(First Washing Step)

The first washing step is a step for conducting liquid sending of a washing liquid after the primary reaction step and before the labeling reaction step. By conducting the first washing step, foreign substances in blood (proteins, sugar lipids and the like other than the analyte) and blood cell components that have been non-specifically adsorbed on the surface of the sensor substrate when the sample is sent in the primary reaction step can be removed. By this way, the further non-specific binding of the labeling antibody used in the labeling reaction step to the above-mentioned non-specifically adsorbed substances and the appearance of the labeled antibody as a noise in the measurement step can be suppressed.

As the washing liquid, general solvents for liquid sending such as PBS (phosphate buffer saline), TBS (tris buffer saline) and the like can be used, and where necessary, a suitable amount of surfactant (for example, Polyoxyethylene (20) Sorbitan Monostearate (trade name: Tween 20)) can be used. The concentration of the surfactant in the washing liquid can be suitably adjusted depending on the kind of the surfactant used, and for example, when the surfactant is "Tween 20", the amount is generally from 0.0001 to 1%, preferably 0.05%.

Furthermore, the conditions such as the flow amount, time and the like in conducting liquid sending by circulating or reciprocating the washing liquid can be suitably preset by using the case when plasma/serum is used as the sample as a standard, and with consideration for an exemplary embodiment of a SPFS measurement system (the sizes of the sensor substrate and flow cell, and the like). The flow amount of the washing liquid is generally from 0.01 to 100 mL/min, preferably from 0.1 to 10 mL/min. Furthermore, the time for conducting the liquid sending of the washing liquid per one washing cycle is generally from 0.5 to 180 minutes, preferably from 5 to 60 minutes.

The first washing step may include one or plural washing treatment(s). Meanwhile, the time during the washing liquid is continuously sent, in other words, the time from the initiation of the liquid sending of the washing liquid to the completion of the liquid sending and the ejection of the washing liquid is counted as one washing treatment. A time for liquid sending of a solvent other than the washing liquid (a solvent for general liquid sending) can be interposed between the two washing treatments, or the washing treatments may be continuously conducted without interposing such time.

According to the finding obtained by the present inventors, the effect of washing is more excellent in the case when multiple washing treatments are conducted with replacing the washing liquid, than in the case when the washing liquid is circulated for a long time per one washing treatment.

The number of times of the washing treatment(s) included in the first washing step can be suitably adjusted with considering the effect of the washing, and is generally from 1 to 10 time(s), preferably from 2 to 8 times.

(Step for Evaluating Blood Cell Component Quantity)

The step for evaluating blood cell component quantity is a step for measuring a blood cell component quantity in a washing liquid and determining whether or not additional washing should be conducted based on the measurement result thereof, and includes a step for measuring a blood cell component quantity in a washing liquid, and a step for judging whether or not the blood cell component quantity measured in the step goes beyond a target value A. It is preferable to evaluate the blood cell component quantity in whole blood by measuring the blood cell quantity in the washing liquid in the first washing step, which has a correlation relationship with the measurement result, rather than by measuring the blood cell quantity in the whole blood itself.

The measurement of the quantity of the blood cell component contained in the washing liquid is not especially limited, and can be conducted by various methods, and for example, it is convenient and preferable to conduct by a method of measuring an OD (Optical Density: optical concentration) of the washing liquid, or the like. In addition, it is also possible to use a RF/DC detection process, a flow-cytometry using a semiconductor laser, or the like.

Specifically, the OD (Optical Density: optical concentration) of the washing liquid is measured by, for example, measuring the OD of the washing liquid at 550 nm (the absorption wavelength of the blood cell component).

FIG. 1 shows a flow of respective steps in an example of the evaluation of the blood cell component quantity by measuring the OD of the washing liquid in the first washing step. In this example, when the measured value of the blood cell component quantity in the washing liquid is higher than a target value A ("YES" in FIG. 1), washing is conducted after returning to the above-mentioned first washing step, and a step for evaluating a blood cell component quantity is conducted again after the completion of the first washing step. This cycle is repeated until the OD becomes the target value A or less ("NO" in FIG. 1). Meanwhile, it is also possible to conduct the step for evaluating the blood cell component quantity by obtaining a difference or ratio of an OD of a wavelength that is absorbed by the blood cell component (for example, 550 nm) and an OD of a wavelength that is not absorbed by the blood cell component (for example, 700 nm). That the measured value of the OD is high means that the washing liquid contains much blood cell component or foreign substances in blood, and thus reflects a much amount of non-specifically adsorbed substances on the sensor substrate, which may be incorporated in the measurement liquid during the photometric condition setting step for the SPFS measurement. When the measured value of the OD becomes a target value or less by conducting additional washing(s), it is presumed that the blood cell components and the like adsorbed on the sensor substrate or the wall surface of the flow path are removed by the washing, and thus the incorporation into the measurement liquid in the photometric condition setting step for the SPFS measurement is suppressed. The target value A of the OD is not especially limited, and can be suitably preset depending on the desired degree of suppression of the incorporation of the blood cell components or foreign substances in blood, and may be preset, for example in the range of from 0.01 to 1.0, preferably from 0.1 to 0.7.

The method for measuring the OD is not especially limited and known various means can be used, and for example, the measurement can be conducted by an assay system using similar units to those of a general spectrometer (a container for housing a sample, a white light source lamp, a prism, a slit, a light detector and the like). In addition, for the target value in the step for evaluating a blood cell component quantity in the case when the blood cell component quantity is measured by a method other than the method of measuring an OD (a RF/DC detection process or the like), the presence or absence of necessity of rewashing can be judged by using a blood cell component quantity that is equivalent to the target value A (OD value) in the OD measurement as a target value.

Figure 2:
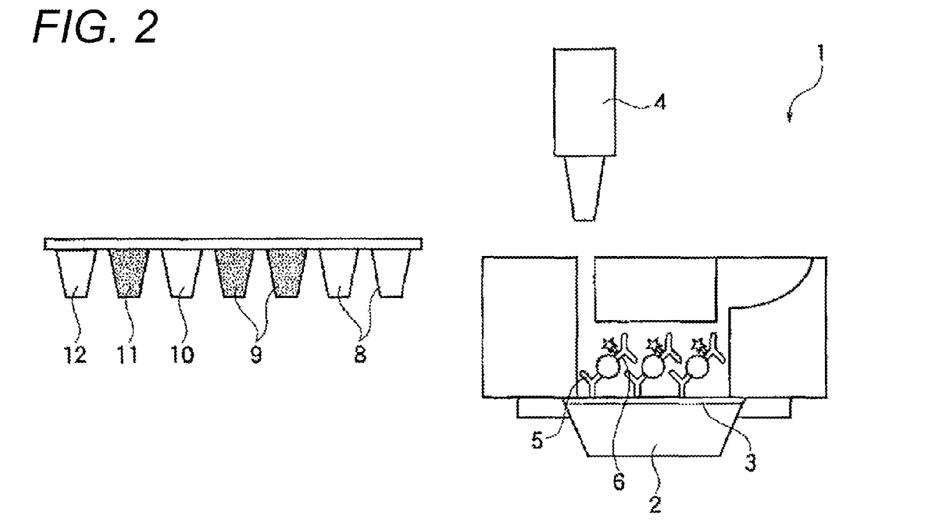
FIG. 2 is a schematic view that schematically shows a position of a liquid sending station position in a whole blood SPFS assay system.
Figure 4:
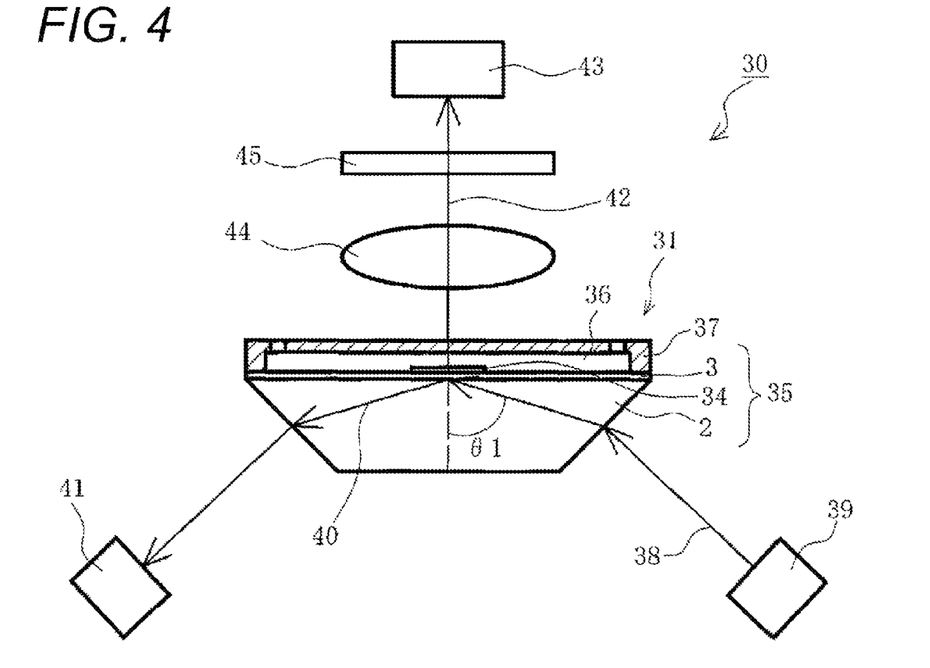
FIG. 4 is a schematic view that schematically shows a measurement station of a whole blood SPFS assay system.

FIG. 2 is a schematic view that schematically shows a liquid sending station of a whole blood SPFS assay system 1, and FIG. 4 is a schematic view that schematically shows a measurement station 30 of the whole blood SPFS assay system 1 in FIG. 2. Although the appearance of a sensor chip 31 is shown to be slightly different between FIGS. 2 and 4, one common sensor chip 31 can be used.

Furthermore, although it is also possible to respectively incorporate a liquid sending station and a measurement station in apparatuses that are different from each other to thereby constitute a whole blood SPFS assay system, it is preferable to constitute by disposing a liquid sending station and a measurement station in one SPFS measurement apparatus so that a liquid is transferred between the two stations by being transferred through, for example, the sensor chip 31.

The sensor chip 31 includes a prism, which is a dielectric element 2, a metal thin film 3 formed thereon, a ligand immobilized area 34 on the metal thin film 3, a ligand (primary antibody) 5 immobilized on the ligand immobilized area 34, and a flow path 36 for the liquid sending of respective reagents to the ligand immobilized area 34.

A pump 4 is disposed in the liquid sending station of the whole blood SPFS assay system 1, and reagents in reagent chips in which various reagents such as a sample 12, dilution liquid 11, labeled antibody solution 10 and washing liquid 9 are filled are sent to the flow path 36 of the sensor chip 31 by using this pump 4. After the liquid sending of the sample 12 to the flow path 36, the washing liquid 9 is sent by using the pump 4 and the OD is measured before the liquid sending of the labeled antibody solution 10. This measurement of the OD can be carried out in various embodiments. For example, an exemplary embodiment in the state that the washing liquid is filled in the flow path 36 or a well having the ligand immobilized area 34 on which the ligand (primary antibody) is immobilized in the sensor chip 31, the OD of the washing liquid is measured, may be exemplified. Furthermore, an exemplary embodiment in which the OD of the washing liquid is measured at around a flow outlet at the downstream side of the ligand immobilized area 34 may also be exemplified. On the other hand, an exemplary embodiment in which an OD relating to a used washing liquid (waste liquid) is measured with intending for the used washing liquid discharged from the sensor chip 31 and stored in a waste liquid container 8, rather than the washing liquid (internal liquid) in the sensor chip 31 as in these methods, for example, in the process of the transferring from the sensor chip 31 to the waste liquid container 8, or after the housing in the waste liquid container 8, may also be exemplified. The OD may be measured in a suitable embodiment with considering for how a unit for measuring the OD is disposed in the SPFS measurement apparatus or whole blood SPFS assay system, and the like.

In addition, the quantity of the blood cell component contained in the washing liquid 9 or the like may be measured instead of the measurement of the OD, by disposing a device for conducting the above-mentioned RF/DC detection process, or a device for conducting a flowcytometry using a semiconductor laser, instead of the above-mentioned unit for measuring an OD.

(Step of Setting SPFS Photometric Conditions)

The step for setting SPFS photometric conditions is a step for setting various photometric conditions for the measurement of SPFS, such as determination of an incident angle for irradiating excited light in the measurement step (a resonance angle for generating surface plasmon resonance), and measurement of an optical blank for correcting a signal measured in the measurement step (background signal) in advance.

The step for setting SPFS photometric conditions is generally conducted on respective samples. However, in the case when a setting that is common in plural samples having similar characteristics is used for a rapid measurement, it is also possible to conduct the step on representative samples and not conduct the step on the other samples. In such case, the above-mentioned step for evaluating the blood cell component quantity may be conducted on only the representative samples during the time from the primary reaction step to the step for setting SPFS photometric conditions, but the first washing step on the other samples is conducted under similar conditions to those for the representative samples.

(Labeling Reaction Step)

The labeling reaction step is a step for bringing a labeled antibody labeled with a fluorescent substance into contact with the sensor substrate. In the case when an antigen has bound to the immobilized antibody on the surface of the sensor substrate to thereby form a complex in the primary reaction step, the labeled antibody further binds to the captured antigen to form a complex formed of the immobilized antibody—the antigen—the labeled antibody. This step can be conducted in accordance with a general SPFS measurement system. FIG. 2 shows a state in which labeled ligand 6, which is a labeled antibody, is bound through an antigen to the ligand 5, which is immobilized antibody.

(Second Washing Step)

The second washing step is a step for conducting liquid sending of a washing liquid after the labeling reaction step and before the measurement step. By conducting the second washing step, the labeled antibody that has been non-specifically adsorbed on the surface of the sensor substrate in the labeling reaction step can be removed, thereby the appearance of the labeled antibody as a noise in the measuring can be suppressed.

The kind and concentration of the surfactant, the flow amount, the time and the like in the liquid sending of the washing liquid in the second washing step can be similar to those in the first washing step, or different conditions may be set as necessary.

(Measurement Step)

In the SPFS measurement system, the measurement step is a step in which light having a specific excitation wavelength is irradiated from the rear surface of the sensor substrate, and the intensity of the light having a specific fluorescence wavelength generated by the irradiation is measured by a light amount detection sensor such as a PMT (photomultiplier tube) disposed on the upper surface of the sensor substrate. If a predetermined analyte (antigen) is present in the sample and an immobilized antibody-antigen-labeled antibody has been formed in the labeling reaction step, the fluorescence emitted by the fluorescent substance in the complex by being excited by an enhanced evanescent wave by SPFS can be measured by a PMT or the like. This step can be conducted according to a general SPFS measurement system. The result of the measurement of the fluorescence amount is output and analyzed by a suitable information processing means, and a quantitative or qualitative analysis of the analyte in the sample can be conducted based on the measurement result.

In the case when whole blood is used as a sample, a certain volume in the whole blood sample is occupied by blood cell components, and thus the volume in which the analyte (antigen) is included is apart of the sample (roughly estimated by total volume×(100−hematocrit value (%))). Furthermore, as shown in the exemplary embodiment mentioned below, in the case when whole blood is used as a sample, a dilution rate that is different from that in the case when serum or plasma is used as a sample is sometimes used. With consideration for such difference, it is desirable to calculate the concentration of the analyte after conducting suitable arithmetic processings for the case when whole blood is used as a sample and the case when serum or plasma is used as a sample, respectively.

<Sensor Substrate>

The sensor substrate is constituted by at least a dielectric element (a prism or a transparent plane substrate), a metal thin film formed on the upper layer of the dielectric element, and a layer including an immobilized ligand formed on the upper layer of the metal thin film (reaction layer).

The metal thin film and the like may be directly formed on the horizontal plane of the prism, but considering the convenience for analyzing many samples and the like, it is desirable that they are formed on one surface of the removable transparent plane substrate that can be attached to and detached from the horizontal plane of the prism. Furthermore, the reaction layer may be directly formed on the surface of the metal thin film, but where necessary, a spacer layer and/or SAM formed of a dielectric may be formed on the metal thin film, and the reaction layer may be formed thereon.

The sensor substrate can be used in combination with elements that form "flow path" (sheets for forming the side walls of the flow path, top panels and the like) for storing various fluids used for the measurement such as SPFS (a sample liquid, a labeled ligand solution, a measuring liquid and the like) and for enabling liquid sending by allowing communication among the respective areas. These can be integrated to give an embodiment of a chip-like structure (sometimes referred to as "sensor chip"). Furthermore, an opening for introducing or ejecting a fluid is formed on the sensor chip, and the opening can be used so as to allow the coming and going of the fluid between the outside and the sensor chip, by using a pump, and for example, a tube having an approximately oval cross-sectional surface which is formed by a soft element (silicone rubber or the like), or the like. The conditions at this time (the flow, time and temperature, and the concentrations of the subject and labeled ligand) can be suitably adjusted.

The sensor substrate or sensor chip can be prepared as follows: in small-lot production (laboratory level), for example, a sensor substrate on which a metal thin film and the like are formed is made in advance, and a sheet or O-ring made of a silicone rubber having a hole having optional shape and size on the center part and a predetermined thickness (the height of a flow path) is put on the surface of the sensor substrate on which the metal thin film and the like have been formed, whereby a side surface structure of a flow path is formed. A light transmittable top panel on which a liquid sending introduction port and a liquid sending ejection port have been formed is then put on the flow path to form a ceiling surface of the flow path, and these are subjected to compression bonding and immobilized by attachments such as screws, whereby the surface plasmon sensor or sensor chip can be prepared. Furthermore, in large-lot industrial production (factory level), the sensor chip can be prepared by, for example, forming a metal thin film, a reaction layer and the like on a predetermined region of a transparent plane substrate to give a sensor substrate, while forming a top panel and a side wall element by forming fine concaves and convexes by mold processing of a plastic, photolithography or the like, and combining these.

(Dielectric Element)

As the dielectric element used for the sensor chip (sensor substrate), dielectric elements made of glass, and plastics such as polycarbonate (PC), cycloolefin polymer (COP) and the like, preferably dielectric elements made of a material having a refractive index [$n_d$] in the range of from 1.40 to 2.20 at d ray (588 nm), can be used. The thickness in the case when a transparent plane substrate is used as the dielectric element can be adjusted in the range of, for example, from 0.01 to 10 mm. Furthermore, it is preferable that the surface of the dielectric element has undergone a washing treatment with an acid or plasma before the formation of the metal thin film.

(Metal Thin Film)

The metal thin film of the sensor chip (sensor substrate) is preferably formed of at least one kind of metal (the metal may be in the form of an alloy) selected from the group consisting of gold, silver, aluminum, copper and platinum, which are stable against oxidation and have a high effect of enhancing electrical field by surface plasmon, and is especially preferably formed of gold. In the case when a plane substrate made of glass is used as the transparent plane substrate, it is preferable to form a thin film of chromium, nickel-chromium alloy or titanium so as to bond the glass and the above-mentioned metal thin film more tightly.

Examples of the method for forming the metal thin film include a sputtering process, deposition processes (resistance heating deposition process, an electron beam deposition process the like), electrolytic plating, a non-electrolytic plating process and the like. It is preferable to form the thin film of chromium and the metal thin film by a sputtering process or a deposition process since the conditions for the formation of the thin film are easily adjusted.

In order to allow easy generation of surface plasmon, the thicknesses of the metal thin films formed of gold, silver, aluminum, copper, platinum, or alloys thereof are each preferably from 5 to 500 nm, and the thickness of the chromium thin film is preferably from 1 to 20 nm. In view of an electrical field-enhancing effect, it is more preferable that the thicknesses are such that gold: from 20 to 70 nm, silver: from 20 to 70 nm, aluminum: from 10 to 50 nm, copper: from 20 to 70 nm, platinum: from 20 to 70 nm and alloys thereof: from 10 to 70 nm, and the thickness of the chromium thin film is more preferably from 1 to 3 nm.

(Spacer Layer)

For the sensor chip (sensor substrate), where necessary, a spacer layer formed of a dielectric may be formed between the metal thin film and the reaction layer (or SAM) so as to prevent metal quenching of fluorescent pigments by the metal thin film.

As the dielectric, optically transparent various inorganic substances, and natural or synthetic polymers can be used. Among these, it is preferable to use silicon dioxide ($SiO_2$) or titanium dioxide ($TiO_2$) since these are excellent in chemical stability, production stability and optical transparency.

The thickness of the spacer layer is generally from 10 nm to 1 mm, and is preferably 30 nm or less, more preferably from 10 to 20 nm in view of resonance angle stability. On the other hand, the thickness is preferably from 200 nm to 1 mm in view of an electrical field-enhancing effect, and more preferably from 400 nm to 1,600 nm in view of the stability of the electrical field-enhancing effect.

Examples of the method for forming the spacer layer formed of a dielectric include a sputtering process, an electron beam deposition process, a thermal deposition process, a formation method by a chemical reaction using a material such as a polysilazane, or application by a spin coater, and the like.

(SAM)

For the sensor chip (sensor substrate), where necessary, a SAM (Self-Assembled Monolayer) may be formed between the metal thin film (or a spacer layer) and the reaction layer.

As the molecule for constituting the SAM, a compound having a functional group that can bind to the metal thin film and the like (a silanol group, a thiol group or the like) on one terminal of the molecule and having a reactive functional group that can bind to the molecule that constitutes the reaction layer (an amino group, a carboxyl group, glycidyl group or the like) on the other terminal is used. Such compound can be easily obtained as a silane coupling agent or a SAM forming agent. For example, carboxyalkanethiols having a carbon atom number of about 4 to 20 (10-carboxy-1-decanethiol and the like) are preferable since they can form a SAM having low optical effects, i.e., high transparency, low refractive index and thin film thickness. The SAM can be formed by bringing a solution of a molecule that constitutes the SAM (an ethanol solution or the like) into contact with the metal thin film and the like, and binding one functional group of this molecule to the metal thin film and the like.

<SPFS Measurement>

A schematic view of the measurement station 30 in a whole blood SPFS assay system based on the principle of surface plasmon-field enhanced fluorescence spectroscopy (SPFS) is shown in FIG. 4. FIG. 4 shows a state in which the sensor chip 31 is loaded in the measurement station 30. The embodiment is not limited to an embodiment in which the sensor chip 31 is detachably constituted and the sensor chip is replaced in every measurement, and may be an embodiment in which the sensor chip 31 is disposed on the whole blood SPFS assay system. The sensor chip 31 here includes the dielectric element 2, the metal thin film 3 formed thereon, a sensor substrate 35 having the ligand immobilized area 34 on the metal thin film 3, and a flow path constituting element 37 that constitutes the flow path 36 that is immobilized on the sensor substrate 35 and enables circulation of various reagent solutions such as a sample on the ligand immobilized area 34.

In a state that the sensor chip 31 constituted by this way is loaded in the measurement station 30, the measurement station 30 includes light source 39 that emits excited light 38 towards the metal thin film 3 on the side of the dielectric element 2 of the sensor chip 31, and light receiving means 41 that receives reflected light 40 that has been emitted from the light source 39 and reflected on the metal thin film 3.

On the other hand, light detection means 43 that receives fluorescence 42 emitted by a fluorescent substance that has labeled an analyte captured on the ligand immobilized area 34 is disposed on the side of the flow path constituting element 37 of the sensor chip 31.

In addition, it is preferable to dispose a light collecting element 44 for efficiently collecting the fluorescence 42 and a wavelength-selecting functional element 45 that removes contained lights other than the fluorescence 42 and select only the necessary fluorescence 42 between the flow path constituting element 37 and the light detection means 43, and an embodiment including those elements is shown in FIG. 4.

Furthermore, in the measurement station 30, a sample containing an intended analyte is allowed to flow into the flow path 36 having the ligand (primary antibody) 3 in the ligand immobilized area 34 on the metal thin film 3 to make the ligand to capture the analyte, the excited light 38 is emitted to the dielectric element 2 from the light source 39 in the state that the captured analyte is labeled with a fluorescent substance, and this excited light 38 enters into the metal thin film 3 at resonance angle $\theta 1$, whereby a compressional wave (surface plasmon) is generated on the metal thin film 3.

In the generation of the compressional wave (surface plasmon) on the metal thin film 3, the excited light 38 and the electronic oscillation in the metal thin film 3 are coupled, and decrease in the light amount of the reflected light 40 is generated. Therefore, if a point where the signal of the reflected light 40 light received by the receiving means 41 changes (the light amount is decreased) is found, the resonance angle $\theta 1$ at which the compressional wave (surface plasmon) is generated can be obtained.

Due to this phenomenon of generation of a compressional wave (surface plasmon), the fluorescent substance at the ligand immobilized area 34 on the metal thin film 3 is efficiently excited, whereby the light amount of the fluorescence 42 emitted from the fluorescent substance is increased.

By receiving this increased fluorescence 42 by the light detection means 43 through the light collecting element 44 and the wavelength-selecting functional element 45, an extremely trace amount and/or extremely low concentration of analyte can be detected.

<Measuring Method>

(Sample)

The sample is a substance that is subjected to a SPFS measurement, and typical samples include samples derived from a blood subject (whole blood, serum, plasma and the like) collected from human, mammals other than human (model animals, pet animals the like) and other animals. During the analysis, where necessary, the sample may be mixed with pure water, saline, buffer, various solvents such as reagent solutions and used, or blood subjects may be mixed with an anticoagulant (heparin or the like) or the like and used. Either of such mixed liquid or sample itself, or a solution containing an analyte, which is prepared for a certain purpose, and fluids that are sent to a predetermined region of the sensor substrate for measuring a signal by a SPFS measurement (this includes a solution, a suspension liquid, a sol, and other substances having fluidity) are encompassed in the sample.

(Analyte)

A substance to be quantified or detected by a SPFS measurement refers to "analyte". Any substance that can be captured by the surface of the sensor substrate can be an analyte without special limitation, and typical analytes include proteins (including polypeptides, oligopeptides and the like) or complexes thereof that serve as tumor markers. Furthermore, cells, viruses and the like having sites that are recognized by ligands (epitopes and the like) on the surface may also be analytes. Furthermore, it is also possible to use other molecules such as nucleic acids (including single chain or double chain DNAs, RNAs, polynucleotides, oligonucleotides, PNAs (peptide nucleic acids) and the like), saccharides (including oligosaccharides, polysaccharides, sugar chains and the like), and lipids as analytes after subjecting to a treatment such as biotinization as necessary.

(Ligand)

A molecule that can specifically bind to the analyte refers to "ligand". Specifically, a ligand immobilized on the surface of a sensor substrate, which is for capturing the analyte on the surface of the sensor substrate, refers to "immobilized ligand" (if the ligand is an antibody, the ligand refers to "immobilized antibody"), and a ligand that is bound to a fluorescent dye, which is present in a liquid for labeling an analyte, refers to "labeled ligand" (if the ligand is an antibody, the ligand refers to "labeled antibody"). The ligand parts of the immobilized ligand and labeled ligand may be the same or different. However, in the case when the immobilized ligand is a polyclonal antibody, the labeled ligand may be either a monoclonal antibody or a polyclonal antibody, whereas in the case when the immobilized ligand is a monoclonal antibody, it is desirable that the labeled ligand is a monoclonal antibody or polyclonal antibody that recognizes an epitope that is not recognized by the immobilized ligand.

As the ligand, a suitable ligand may be selected in accordance with the analyte to be captured, and antibodies, receptors, other specific molecules (such as avidin for capturing a biotinylated analyte) and the like, which can specifically bind to a predetermined site of the analyte, can be used as the ligand.

The method for disposing the ligand on the surface of the sensor substrate is not especially limited, and typically, a method such that the functional group possessed by the ligand and the functional group possessed by the SAM-forming molecule (a silane coupling agent or the like) are bonded in accordance with a known means such as an amine coupling process, a thiol coupling process and an indirect capture process (capture process) to thereby connect the ligand to the metal thin film (or a spacer layer) via the SAM-forming molecule. For example, in the amine coupling process, a water-soluble carbodiimide (WSC) such as 1-ethyl-3-(3-dimethylaminopropyl) carbodiimide hydrochloride (EDC) and N-hydroxysuccinic acid imide (NHS) are reacted to activate the carboxyl group of the SAM (the NHS is introduced), and a ligand having an amino group is reacted, whereby the ligand is bonded to the SAM through the NHS.

In addition, in order to prevent the nonspecific adsorption of the analyte, it is preferable to immobilize the above-mentioned ligand on the surface of the sensor substrate to immobilize the ligand, and then treat the surface of the sensor, the side walls and top panel of the flow path, and the like with a blocking agent such as bovine serum albumin (BSA).

On the other hand, the labeled ligand can be prepared in a similar manner to that for a complex (conjugate) of a ligand and a fluorescent dye, which is also used in a general immunostaining process. For example, by respectively preparing a complex of a ligand and an avidin (including streptavidin and the like) and a complex of a fluorescent dye and biotin, and reacting these complexes, a complex in which the fluorescent dye is bound to the ligand via the avidin/biotin (four biotins at the maximum can bind to one avidin) can be obtained. Besides the reaction of biotin and avidin as mentioned above, a manner of reaction of a primary antibody—a secondary antibody used in a fluorescence labeling process, or reactions between a carboxyl group and an amino group, between an isothiocyanate and an amino group, between a sulfonyl halide and an amino group, between an iodoacetamide and a thiol group, and the like may also be used.

<Spectrometer>

Figure 3:
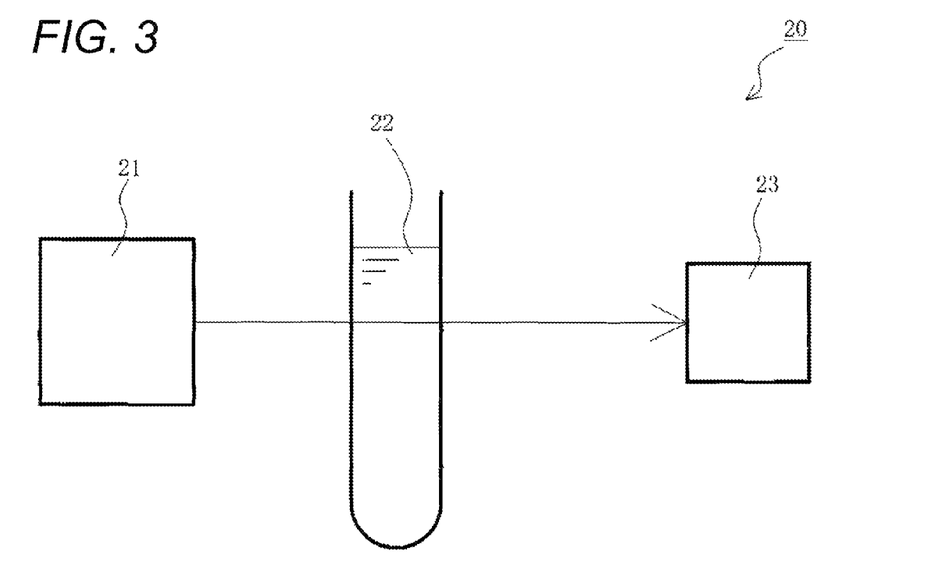
FIG. 3 is a schematic view showing a spectrometer.

As shown in FIG. 3, a spectrometer 20 is composed of a spectrometric unit 21 that is configured to separate light that has entered from a light source depending on respective wavelengths, and a spectrometer 23, which is a unit configured to emit the separated light to liquid to be evaluated 22 and measure the degree of the attenuation of the light. A transmittance is obtained from the intensity of the light emitted to the liquid to be evaluated 22 and the intensity of the light that has passed the liquid to be evaluated 22, and a light absorbance is obtained from the transmittance.

EXAMPLES

A further specific explanation will be made according to the following Examples. The present invention is not construed to be limited to the descriptions of the following Examples unless the present invention goes beyond the gist thereof.

Based on basic data, a blood cell component residual rate in a washing residual liquid of 1% is temporarily preset as a threshold value, and the condition is preset to a blood cell component residual rate in the washing residual liquid of lower than 1%.

An optical blank value is a background of a finally obtained signal, and if this value fluctuates, then a quantitative value deviates from an original quantitative value.

The resonance angle is represented by a difference from Comparative Example 1 as a standard.

Example 1

A whole blood sample (sample) was prepared, and as shown in the flow in FIG. 1, a primary reaction step in a SPFS measurement was conducted by liquid sending for 10 min. After the sample had undergone the first washing step, a first washing step by liquid sending of a washing liquid and a step for measuring a light absorbance of the washing residual liquid were repeatedly conducted until the light absorbance OD 540 of the washing residual liquid at 550 nm (the absorption wavelength of the blood cell component) became not more than 0.4 (the blood cell component residual rate in the washing residual liquid is 1%) ("NO" in FIG. 1) ("YES" in FIG. 1). Thereafter measurements of a resonance angle and an optical blank, which are photometric conditions, were conducted. The above-mentioned operations were repeatedly conducted six times (n=6). The results are shown in Table 1.

TABLE 1

|  | Sample species | Resonance angle | Optical blank |
|---|---|---|---|
| Example 1 | Whole blood | −0.03 | 6362 counts |
| Comparative Example 1 | Plasma | — | 5681 counts |
| Comparative Example 2 | Whole blood | 0.32 | 11753 counts |

Comparative Example 1

A plasma sample was prepared, and a primary reaction by liquid sending for 10 min and a washing operation of a SPFS immunoassay were conducted. Subsequently, measurements of a resonance angle and an optical blank, which are photometric conditions, were conducted.

Comparative Example 2

A whole blood sample was prepared, and a primary reaction by liquid sending for 10 min and a washing operation of a SPFS immunoassay were conducted. The OD540 average value of the washing residual liquid was 2.26. Subsequently, measurements of a resonance angle and an optical blank, which are photometric conditions, were conducted.

The above-mentioned operations were repeatedly conducted six times (n=6). The results are shown in Table 1.

Figure 5:
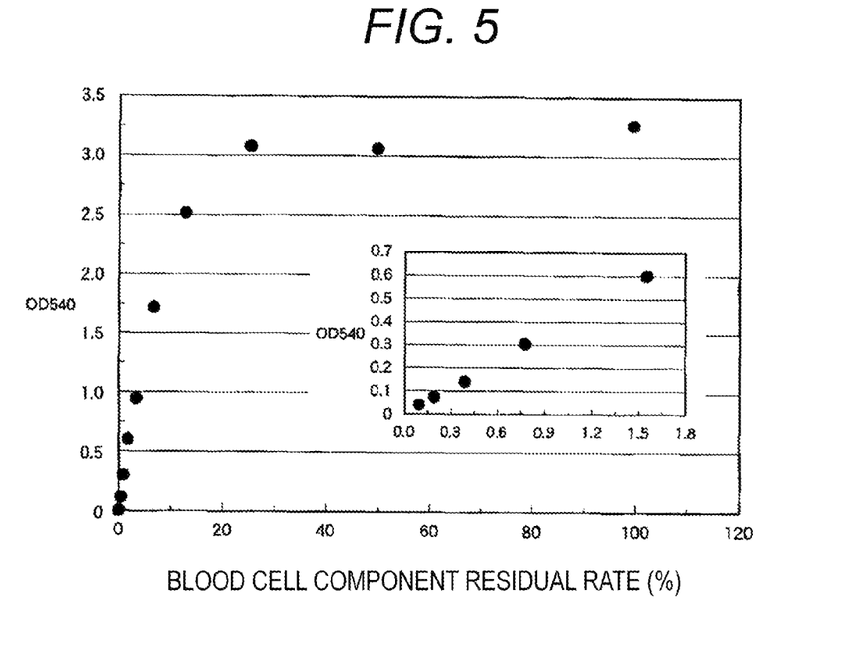
FIG. 5 is a drawing showing a result of a light absorbance measurement of a whole blood sample.

FIG. 5 shows the result of the measurement of the light absorbance of the whole blood sample. The horizontal axis of FIG. 5 represents the residual rate of the blood cell component (%), and the longitudinal axis represents the light absorbance OD540. The drawing in FIG. 5 is an enlarged drawing for the blood cell component residual rates in the range of from 0 to 1.8%.

The condition for the measurement of the light absorbance was such that the whole blood sample was diluted with a washing liquid. The washing liquid was TBST (a TBS buffer solution containing 0.05% of a surfactant: Tween 20), and a part of the blood cell component in the whole blood had been hemolyzed (the cell membrane had been broken, and the content had been eluted into the solution).

From FIG. 5, when the blood cell component residual rate was 0.1%, ODA540 was 0.04, and ODA540 was 0.07 at 0.2%, ODA540 was 0.13 at 0.4%, ODA540 was 0.3 at 0.8%, ODA540 was 0.6 at 1.6%, ODA540 was 0.9 at 5%, ODA540 was 1.7 at 8.0%, ODA540 was 2.5 at 14.0%, ODA540 was 3.1% at 24%, ODA540 was 3.1 at 50%, and ODA540 was 3.3 at 100%.

It is understood from these results that the resonance angle fluctuation and optical blank value in Example 1 were significantly decreased as compared to those of Comparative Example 2, and were asymptotic to the standard performances of Comparative Example 1, and thus a similar optical measurement to that in the case when plasma is used as a sample, eventually a SPFS measurement, is possible in a SPFS measurement intended for whole blood.

The invention claimed is:

1. An assay method utilizing surface plasmon-field enhanced fluorescence spectroscopy for analyzing a whole blood sample containing an analyte, comprising:
   a primary reaction step comprising contacting the sample with a sensor substrate,
   a subsequent first washing step comprising washing the sensor substrate with a washing liquid,
   a labeling reaction step comprising bringing a fluorescent labeled antibody directed against the analyte into contact with the sensor substrate, which is further conducted after the first washing step, and
   a measurement step for measuring fluorescence generated by fluorescence labeled analyte in a complex on the sensor substrate after the labeling reaction step,
   wherein the method includes a step of evaluating a blood cell component quantity retained on the sensor substrate between the primary reaction step and the labeling reaction step.

2. The assay method utilizing surface plasmon-field enhanced fluorescence spectroscopy according to claim 1, wherein the first washing step is repeated until an index that reflects the blood cell component quantity in the evaluation step reaches a predetermined value.

3. The assay method utilizing surface plasmon-field enhanced fluorescence spectroscopy according to claim 2, wherein a subject to be evaluated of the blood cell component quantity in the evaluation step is a washing liquid in the first washing step.

4. The assay method utilizing surface plasmon-field enhanced fluorescence spectroscopy according to claim 2, wherein the washing liquid in the first washing step is an internal liquid in a sensor chip.

5. The assay method utilizing surface plasmon-field enhanced fluorescence spectroscopy according to claim 2, wherein the washing liquid in the first washing step is a waste liquid discharged from the sensor chip.

6. The assay method utilizing surface plasmon-field enhanced fluorescence spectroscopy according to claim 2, wherein the index that reflects the blood cell component quantity is a measurement value of a light absorbance.

7. The assay method utilizing surface plasmon-field enhanced fluorescence spectroscopy according to claim 6, wherein a subject to be evaluated of the blood cell component quantity in the evaluation step is a washing liquid in the first washing step.

8. The assay method utilizing surface plasmon-field enhanced fluorescence spectroscopy according to claim 6, wherein the washing liquid in the first washing step is an internal liquid in a sensor chip.

9. The assay method utilizing surface plasmon-field enhanced fluorescence spectroscopy according to claim 6, wherein the washing liquid in the first washing step is a waste liquid discharged from the sensor chip.

10. The assay method utilizing surface plasmon-field enhanced fluorescence spectroscopy according to claim 1, wherein the method evaluates the blood cell component quantity in the washing liquid on the sensor substrate.

11. The assay method utilizing surface plasmon-field enhanced fluorescence spectroscopy according to claim 10, wherein the washing liquid in the first washing step is an internal liquid in a sensor chip.

12. The assay method utilizing surface plasmon-field enhanced fluorescence spectroscopy according to claim 10, wherein the washing liquid in the first washing step is a waste liquid discharged from the sensor chip.

13. The assay method utilizing surface plasmon-field enhanced fluorescence spectroscopy according to claim 1, wherein the washing liquid in the first washing step is an internal liquid in a sensor chip.

14. The assay method utilizing surface plasmon-field enhanced fluorescence spectroscopy according to claim 1, wherein the washing liquid in the first washing step is a waste liquid discharged after the first washing step.

15. The assay method utilizing surface plasmon-field enhanced fluorescence spectroscopy according to claim 1, wherein the evaluation step is conducted after the first washing step, an index that reflects the blood cell component quantity in the evaluation step is a measurement value of a light absorbance, and the first washing step is conducted again in the case when the measurement value of a light absorbance goes beyond a predetermined value.

* * * * *